United States Patent [19]

Badoz

[11] Patent Number: 5,647,745
[45] Date of Patent: Jul. 15, 1997

[54] HEAD FOR DENTAL CONTRA-ANGLE

[75] Inventor: Jean-Marie Badoz, Pontarlier, France

[73] Assignee: Micro Mega SA, Besancon, France

[21] Appl. No.: 453,435

[22] Filed: May 30, 1995

Related U.S. Application Data

[63] Continuation of Ser. No. 43,659, Apr. 6, 1993, abandoned.

[30] Foreign Application Priority Data

Apr. 6, 1992 [FR] France ................................. 9204327

[51] Int. Cl.[6] ................................. A61C 1/08
[52] U.S. Cl. ................................. 433/126
[58] Field of Search ................................. 433/114, 125, 433/126, 127, 128, 129, 130, 132, 133

[56] References Cited

U.S. PATENT DOCUMENTS

| | | |
|---|---|---|
| 3,070,381 | 12/1962 | Saffir ................................. 433/127 X |
| 3,098,299 | 7/1963 | Page ................................. 433/127 X |
| 3,381,378 | 5/1968 | Lawrence ................................. 433/127 |
| 3,955,284 | 5/1976 | Balson ................................. 433/126 |
| 4,406,470 | 9/1983 | Kataoka et al. ................................. 433/127 X |
| 4,711,630 | 12/1987 | Durr ................................. 433/29 |
| 4,874,314 | 10/1989 | Fleer et al. ................................. 433/127 X |
| 5,028,233 | 7/1991 | Witherby ................................. 433/114 |
| 5,156,547 | 10/1992 | Bailey ................................. 433/125 |
| 5,160,263 | 11/1992 | Meller et al. ................................. 433/125 |
| 5,209,658 | 5/1993 | Brahler ................................. 433/125 |
| 5,252,067 | 10/1993 | Kakimoto ................................. 433/126 X |
| 5,308,242 | 5/1994 | McLaughlin et al. ................................. 433/114 |

*Primary Examiner*—Nicholas D. Lucchesi
*Attorney, Agent, or Firm*—Weiser & Associates, P.C.

[57] ABSTRACT

A head for a dental contra-angle having an operating shaft is coupled to the operating shaft in the vicinity of the bend of the contra-angle. The head is produced principally from a synthetic material and comprises an element for fastening the head onto the contra-angle, a pinion engaging a drive shaft associated with the head, and a support for receiving a tool and for locking the tool in the head. These various elements are designed so that the head can be sterilized or disposed of after use.

22 Claims, 3 Drawing Sheets

1

HEAD FOR DENTAL CONTRA-ANGLE

This application is a continuation of application Ser. No. 08/043,659 filed Apr. 6, 1993 now abandoned.

BACKGROUND OF THE INVENTION

The present invention relates to the field of contra-angles, and more particularly, to that of heads for contra-angles of the type which are interchangeable and of low cost.

Preventing the risks of cross-contamination in the dental suite is of increasing concern for practitioners. In order to combat this risk, the dentist has available conventional sterilisation means such as autoclaves or disinfection by devices such as the one described in Patent FR 2,618,357. In the case of autoclaves, the sterilisation operations are time consuming and therefore expensive.

The apparatus according to Patent FR 2,618,357 provides a rapid and economical solution, but one which nevertheless requires additional investment on the part of the practitioner.

An effective solution for preventing cross-contamination is described in Patents U.S. Pat. No. 5,020,994 and U.S. Pat. No. 5,007,832. Unfortunately, the solutions provided are applicable only to right-handed pieces which are equipped with a right-angled head intended exclusively for prophylaxis. This does not provide a general solution for dental operations, and in particular, does not allow the fastening of a bur according to the choice of the practitioner.

SUMMARY OF THE INVENTION

The object of the present invention is to provide a contra-angle hand piece of the type used in dentistry, hereinafter referred to as a contra-angle, which is provided with a very low-cost head which allows the dentist either to have available a large number of heads which he may sterilise in large batches, or which are disposable after each operation, and which also make it possible to securely hold the bur or other instruments chosen by the dentist, (who sometimes needs to change them during an operation).

This result is obtained with a head for dental contra-angle comprising a known shaft, wherein the head being coupled to the shaft in the vicinity of the bend of the contra-angle, and wherein the head (1) is produced principally from a synthetic material and comprises:

—an element means for fastening onto the shaft,

—a pinion engaging a drive shaft, and

—a support for the tool and for locking the tool in the head.

These various elements are designed so that the head can be sterilized or disposed of after use.

In association with a contra-angle, the drive shaft of the head may be either fixed to the shaft of the contra-angle or, as a variant, may be integral with the contra-angle head.

Advantageously, the head can include a light guide for illuminating the operation field, as well as, if desired, internal ducts for transporting air and spray water.

Since the head is produced from a synthetic material, all the advantages of injection moulding techniques may be used.

BRIEF DESCRIPTION OF THE DRAWINGS

The present invention will be better understood with reference to the non-limiting description of preferred embodiments which is provided below, taken in conjunction with the following illustrations.

DETAILED DESCRIPTION OF A PREFERRED EMBODIMENT

Figure 1:
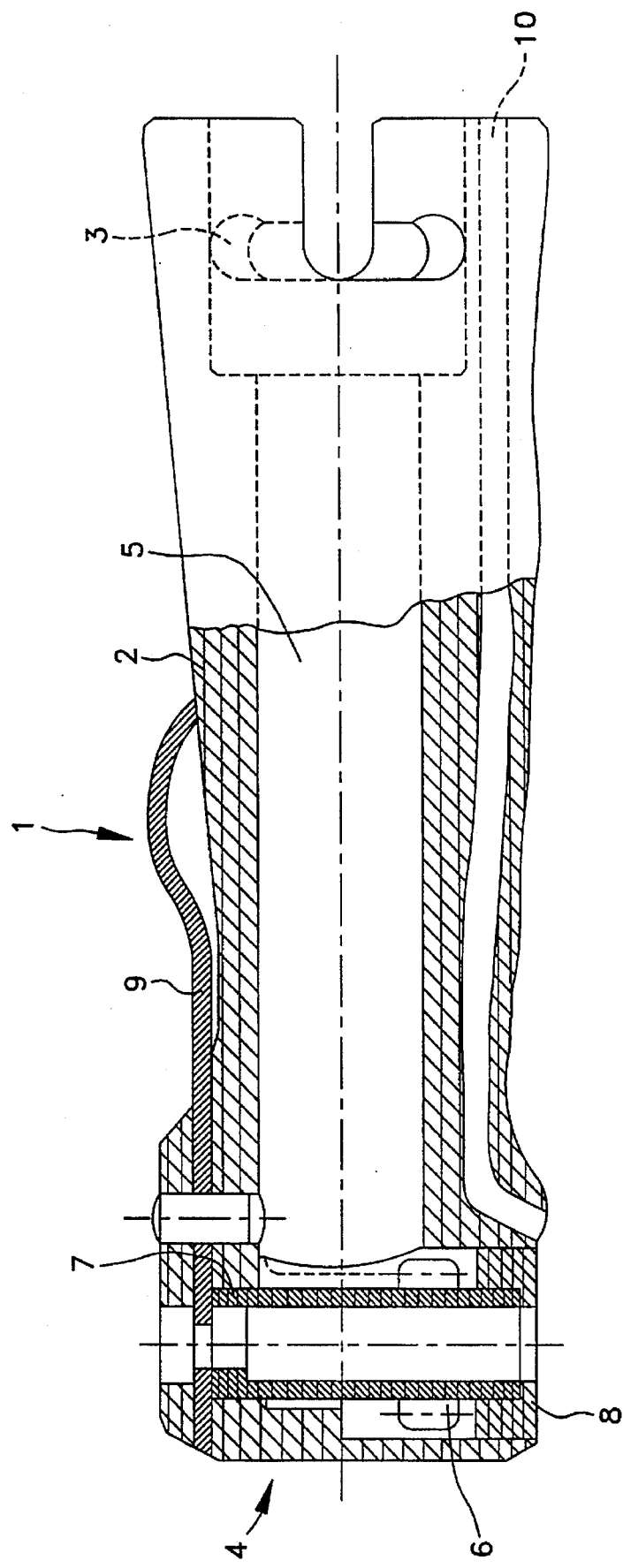
FIG. 1 shows a partial sectional view in side elevation of a contra-angle and head according to the invention.

The head, given the general reference (1), generally comprises:

—an elongate body (2) fitted at its proximal end with a fastening element (3) and at its distal end with a support (4) for a tool, and a pinion (6) for engaging a drive shaft (5) disposed in the body (2) and coupled to a motor (not shown).

Figure 2:
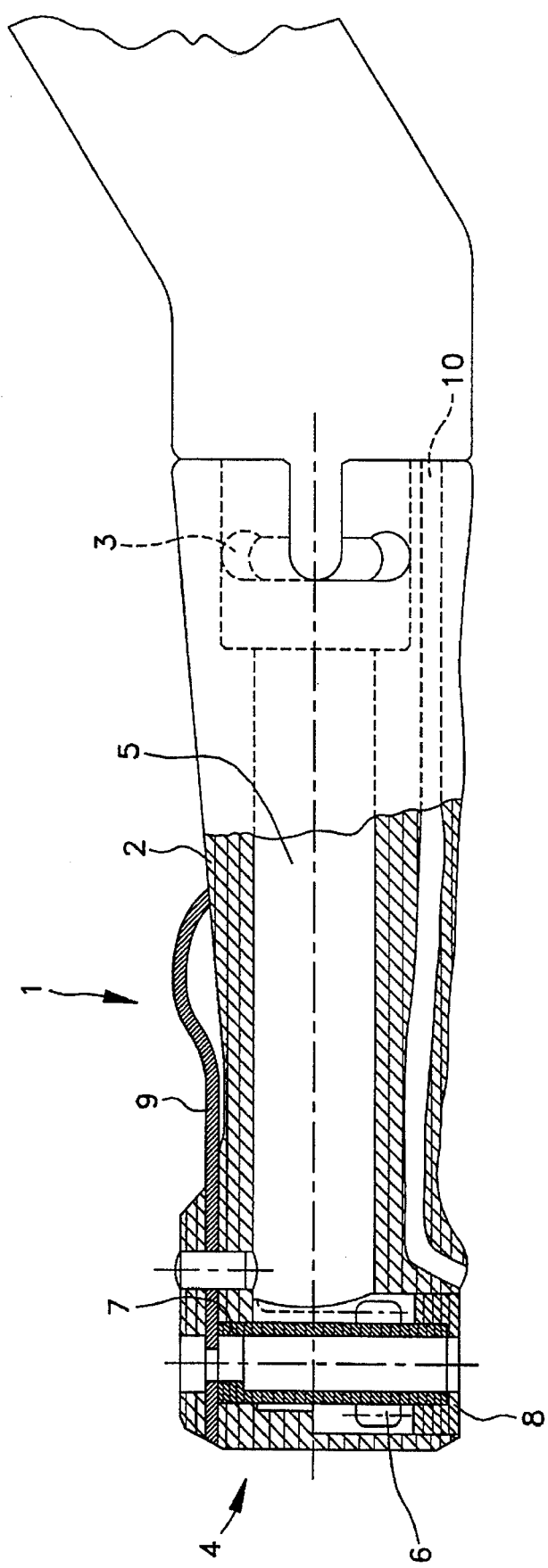
FIG. 2 shows a partial sectional view in side elevation of an alternative embodiment contra-angle and head according to the invention.
Figure 3:
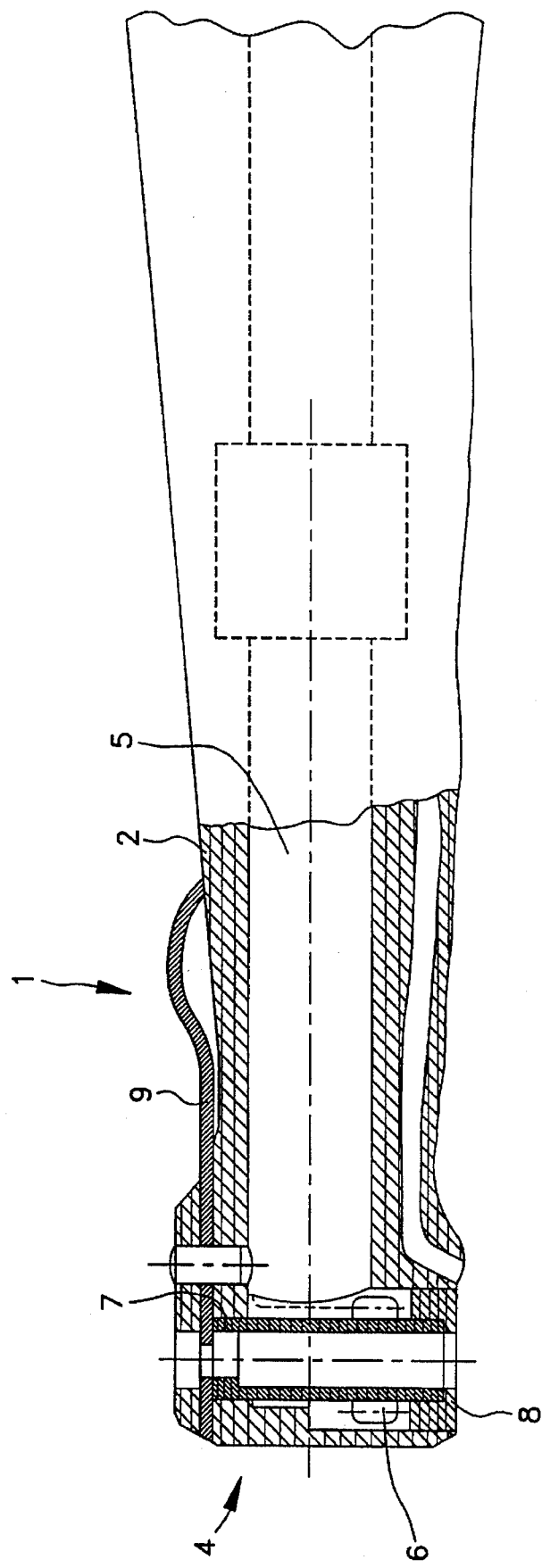
FIG. 3 shows a partial sectional view in side elevation of an integral contra-angle and head according to the invention.

The head (1) may be coupled with either a straight contra-angle (FIG. 1) or a contra-angle including a bend (FIG. 2), or may be integral with the contra-angle (FIG. 3), as desired.

The tool support generally includes a tube (7) moulded from plastic or from "Zamak" (a highly pure zinc alloy further including 3.9 to 4.3% aluminum, 0.03 to 0.6% magnesium and possibly 1.0 to 3.0% copper coated with a self-lubricating layer. The tube (7) is held by a plastic collar (8) which is driven on, welded or machined, and is intended to receive the heads of conventional dental tools. These heads are held using, for example, a conventional latch system (9).

It is possible to provide a longitudinal light guide (10), for example, made from a synthetic material having a lower melting temperature than the material of the head body.

Provisions are also made (which is relatively simple using an injection molding technique) for leaving one or more longitudinal bores for transporting air or water for the spray from corresponding supply lines at the front end of the motor.

The head thus obtained is of low cost, and may be sterilised in large batches (low cost for the practitioner), or disposed of after each patient. Such heads nevertheless have the advantage of being able to hold burs in the conventional manner.

I claim:

1. A head for detachably engaging a dental contra-angle having an operating shaft, the contra-angle including a drive shaft extending along the operating shaft and terminating with a drive gear, wherein the head comprises means associated with a first end for detachably fastening the head to the operating shaft of the contra-angle, a pinion associated with a second end of the head for engaging the drive gear of the drive shaft of the contra-angle, a tube of a defined length associated with and surrounded by the pinion, wherein the tube includes a hollow cavity which extends fully along the length of the tube for detachably supporting a tool, and means for locking the tool in the head, wherein the hollow cavity of the tube extends to the locking means, and wherein the head is formed principally from a synthetic material so that the head can be detached from the contra-angle and sterilized or disposed of after use.

2. The head of claim 1 which further includes a light guide extending along the head, for conveying light to the second end of the head.

3. The head of claim 2 wherein the light guide is formed from a synthetic material having a melting temperature lower than the melting temperature of the synthetic material forming the head.

4. The head of claim 1 which further includes internal ducts extending along the head, for transporting air and spray water to the second end of the head.

5. The head of claim 1 wherein the tube is molded from a synthetic material.

6. The head of claim 5 wherein the synthetic material is a plastic.

7. The head of claim 5 wherein the synthetic material is a zinc alloy.

8. The head of claim 5 wherein the synthetic material further includes a self-lubricating coating layer.

9. The head of claim 5 wherein the tube further includes a collar for holding the tube in the second end of the head.

10. A dental contra-angle having an operating shaft and detachably receiving a head, wherein the contra-angle includes a drive shaft extending along the operating shaft, wherein the drive shaft terminates with a drive gear, and wherein the head comprises means associated with a first end for fastening the head to the operating shaft of the contra-angle, a pinion associated with a second end of the head and engaging the drive gear of the drive shaft of the contra-angle, a tube of a defined length associated with and surrounded by the pinion, wherein the tube includes a hollow cavity which extends fully along the length of the tube for detachably supporting a tool, and means for locking the tool in the head, wherein the hollow cavity of the tube extends to the locking means, and wherein the head is formed principally from a synthetic material so that the head can be detached from the contra-angle and sterilized or disposed of after use.

11. The dental contra-angle of claim 10 wherein the contra-angle includes a bend, and wherein the head is coupled to the contra-angle adjacent to the bend.

12. The dental contra-angle of claim 10 wherein the drive shaft of the head is fixed to the operating shaft of the contra-angle.

13. The dental contra-angle of claim 10 wherein the drive shaft of the head is integral with the operating shaft of the contra-angle.

14. The dental contra-angle of claim 10 which further includes a light guide extending along the head, for conveying light to the second end of the head.

15. The dental contra-angle of claim 14 wherein the light guide is formed from a synthetic material having a melting temperature lower than the melting temperature of the synthetic material forming the head.

16. The dental contra-angle of claim 10 which further includes internal ducts extending along the head, for transporting air and spray water to the second end of the head.

17. The dental contra-angle of claim 10 wherein the tube is molded from a synthetic material.

18. The dental contra-angle of claim 17 wherein the synthetic material is a plastic.

19. The dental contra-angle of claim 17 wherein the synthetic material is a zinc alloy.

20. The dental contra-angle of claim 17 wherein the synthetic material further includes a self-lubricating coating layer.

21. The dental contra-angle of claim 17 wherein the tube further includes a collar for holding the tube in the second end of the head.

22. A head for detachably engaging a dental contra-angle having an operating shaft, wherein the head comprises means associated with a first end for detachably fastening the head to the operating shaft of the contra-angle, a pinion associated with a second end of the head for engaging a drive shaft of the contra-angle, a tube of a defined length associated with and surrounded by the pinion, wherein the tube includes a hollow cavity which extends fully along the length of the tube for detachably supporting a tool, means for locking the tool in the head, wherein the hollow cavity of the tube extends to the locking means, and a light guide extending along the head, for conveying light from the contra-angle to the second end of the head, wherein the head is formed principally from a synthetic material so that the head can be sterilized or disposed of after use.

* * * * *